Figure 1:
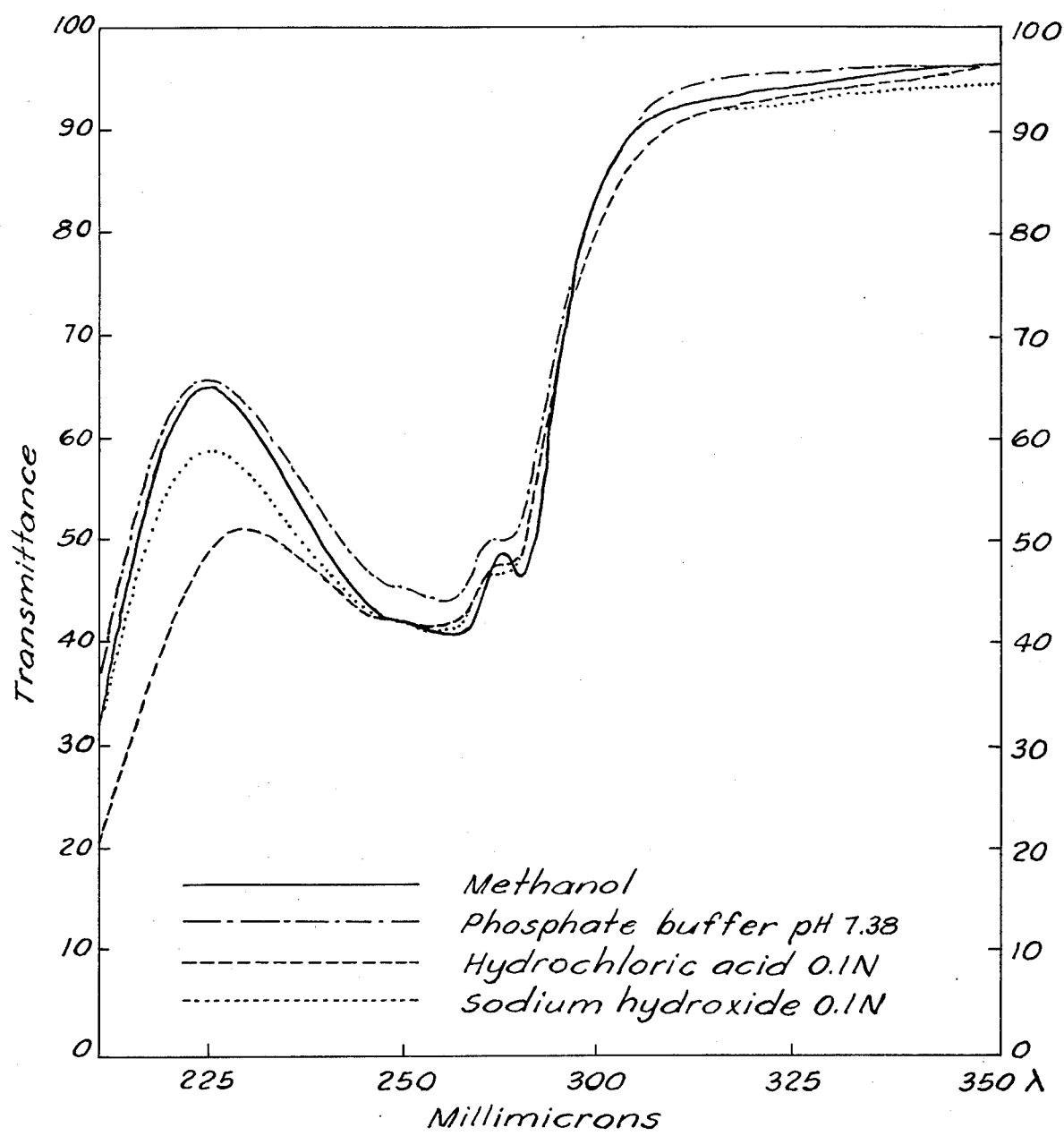

United States Patent [19]

Parenti et al.

[11] 4,022,884
[45] May 10, 1977

[54] GARDIMYCIN AND PROCESS FOR PRODUCING SAME

[75] Inventors: Francesco Parenti; Carolina Coronelli; Giorgio Tamoni, all of Milan; Giancarlo Lancini, Pavia, all of Italy

[73] Assignee: Gruppo Lepetit S.p.A., Milan, Italy

[22] Filed: July 17, 1975

[21] Appl. No.: 596,702

[30] Foreign Application Priority Data

July 27, 1974 United Kingdom ............. 33283/74

[52] U.S. Cl. .............................. 424/117; 195/80 R
[51] Int. Cl.$^2$ ........................................ A61K 35/74

[58] Field of Search ................... 424/117; 195/80 R

[56] References Cited

UNITED STATES PATENTS 3,683,072  8/1972  Miller et al. ........................ 424/117
3,697,646  10/1972  Coronelli et al. .................. 424/117

*Primary Examiner*—Jerome D. Goldberg
*Attorney, Agent, or Firm*—Theodore Post; C. Kenneth Bjork

[57] ABSTRACT

The antibiotic gardimycin and process for producing said antibiotic by fermentation of strains belonging to the genus Actinoplanes.

7 Claims, 2 Drawing Figures

GARDIMYCIN AND PROCESS FOR PRODUCING SAME

The present invention refers to the production and the isolation of a new family of antibiotic substances obtained by fermentation of strains belonging to the genus Actinoplanes. These substances will hereafter be referred to as metabolite A, metabolite B and metabolite C: metabolite B is also named gardimycin.

As stated above the antibiotic substances are produced by cultivation of fermenting strains belonging to the genus Actinoplanes. These strains were isolated from soil samples collected at the localities Temossi (Italy) and Garbadi Bridge (India). Our collection numbers are A/6353 for the strain isolated from the Italian soil sample and A/10889 for the strain isolated from the Indian soil sample: both have been deposited and made part of the stock culture collection of ATCC where they were assigned the numbers 31048 and 31049 respectively.

In the preparation of the new antibiotic substances the selected organism is cultivated under aerobic conditions in an aqueous nutrient medium containing a source of carbon, a source of nitrogen and inorganic salts. Ordinarily the strain is precultured in a shake flask, until substantial antibiotic activity is present, then the culture is used to inoculate jar fermentors containing a nutrient fermentative medium. Cultivation is continued at 25°–35° C under aerobic conditions for a time sufficient to produce a substantial antibiotic level. During this time microbiological assays are carried out by the agar diffusion method to control the concentration of the antibiotic substance produced. *Sarcina lutea* is used as the test organism.

The so obtained antibiotic activity can be isolated from the fermentation broth by conventional procedures, such as, for instance, by extraction with an organic solvent in which the antibiotic activity is soluble and which is immiscible with the aqueous medium. For this purpose, organic solvents selected from lower alkanols of 3 to 6 carbon atoms and ($C_{1-4}$)-lower halogenated hydrocarbons may advantageously be employed.

The organic phase is separated from the aqueous medium, concentrated to small volume and allowed to stand for 10–15 hours at low temperature until a precipitate forms, which is recovered by filtration. Paper chromatography on Whatman paper No. 1 and thin layer chromatography on silicagel of the obtained curde product, and subsequent microbiological development (Nicolaus et al., Il Farmaco, Ed. Prat., 8, 350–370, 1961) on *Staphylococcus aureus* as the detecting system, indicate the presence of at least two active components, which for identification purposes, are named metabolite A and metabolite B, the latter being produced in higher amounts than the former. These two components have different $R_f$ values which vary depending on the nature of the eluting system. Metabolites A and B may be purified and isolated as the pure compounds by means of usual techniques, such as, for instance, by several countercurrent extractions in a predetermined solvent system in which the two antibiotic substances have different partition coefficients. During this step metabolite B is recovered as the monosodium salt, which can in turn be transformed into other salts with alkali or alkali earth metals, or into the corresponding free acid, by means of common operations.

The mother liquors deriving from the butanol extract are poured into an inert, non-polar organic solvent, as, for instance, light petroleum, and a further precipitate forms.

Chromatographic investigations and microbiological developments carried out as above indicate that the obtained solid essentially consists of a single product, which is different from metabolites A and B owing to the different $R_f$ values in the same eluting system: for identification purposes it is named metabolite C. The chromatographic patterns of the three metabolites A, B and C will be hereinafter reported.

Metabolite A, metabolite B (hereafter referred to as gardimycin) as well as its salts with alkali and alkali earth metals and metabolite C show good antibacterial in vitro and in vivo activities. More particularly, gardimycin exhibits an outstanding in vitro antimicrobial action especially against gram-positive bacteria an concentration levels between 1 and 50 $\mu$g/ml, as it results from the following table, reporting the minimal concentration of antibiotic substance which inhibits the growth of various pathogenic microorganisms.

TABLE 1

| Strain | Minimal inhibitory concentration ($\mu$g/ml) |
|---|---|
| Staphylococcus aureus ATCC 538 | 50 |
| Micrococcus flavus ATCC 10240 | 1 |
| Streptococcus faecalis ATCC 10541 | 50 |
| Streptococcus haemolyticus C 203 | 2 |
| Diplococcus pneumoniae UC 41 | 50 |
| Clostridium perfringens ISS 30543 | 2 |
| Neisseria gonorrheae ATCC 9826 | 20 |

Another favorable characteristic of the antibiotic substance gardimycin is that it is active against clinically isolated Streptococcus strains.

TABLE 2

| Strain | | Minimal inhibitory concentration ($\mu$g/ml) |
|---|---|---|
| Streptococcus haemolyticus | 2078 | 1 |
| Streptococcus haemolyticus | 2087 | 1 |
| Streptococcus viridans | 2057 | 5 |
| Streptococuss viridans | 2085 | 2 |

Furthermore, as stated above, gardimycin displays also a very interesting in vivo activity against experimental infections in mice caused by pathogenic bacteria of the genus Diplococcus and Streptococcus. The hereinbelow reported table shows the $ED_{50}$ values of gardimycin against experimental infections provoked by *Streptococcus haemolyticus* C 203 and *Diplococcus pneumoniae* UC 41.

Table 3

| Strain | $ED_{50}$ mg/Kg |
|---|---|
| Streptococcus haemolyticus C 203 | 0.75 |
| Diplococcus pneumoniae UC 41 | 30 |

These favorable antimicrobial properties are coupled with a very low toxicity as the $LD_{50}$ value of the antibiotic gardimycin is higher than 1000 mg/Kg i.p. and about 2000 mg/Kg i.v.

DESCRIPTION OF THE PRODUCING STRAINS

Description of strain A/6353

The strain grows well on several agar media. On oat meal agar the colonies, which are of about 5 mm. in diameter, have indented contours, slight radial furrows and a central depression. Aerial mycelium is always absent. Sporangia form abundantly on oat meal agar, glycerol asparagine agar and Czapek glucose agar, showing different shape and size depending on the medium.

On oat meal agar they have regular contours and a shape varying from spherical to oval. The sporangia size is in the range 15–25 μ. The spores are motile and spherical with a diameter of 1.5–2 μ. A yellow-amber soluble pigment is produced in several media.

Description of Actinoplanes A/10889

The strain grows well on various nutrient agars. The surface is opaque and usually rough to wrinkled. Aerial mycelium is usually absent, however in some media rudiments of aerial mycelium are observed. At the microscopic examination the vegetative mycelium is slightly branched with a diameter of ~1μ. The sporangia form moderately only on calcium malate agar and are globose with irregular surface often lobate, with diameter ranging from 7.0 to 12.0μ. After rupture of the sporangial wall it is possible to observe sporangial release. The subspherical spores are motile (1.0 to 1.5μ diameter).

A comparison of some morphological characteristics of the two strains is shown in table 4.

Table 4

|  | Strains | |
| --- | --- | --- |
|  | A/10889 | A/6353 |
| Sporangia | formed only on Ca malate agar Size: 7×12 mμ | formed abundantly on several agars; but variable in size and shape. On oat meal agar the size is 15–25 mμ |
| Spores | subspherical (1 to 1.5 μm) | spherical (1.5–2 mμ) |
| Aerial mycelium | rudimentary | always absent |
| Soluble pigment | absent | yellow-amber pigment present on some agars |

Table 5 reports the cultural characteristics of Actinoplanes A/6353 and Actinoplanes A/10889 cultivated on various standard media suggested by Shirling and Gottlieb (Intern.J.Syst.Bact. 16, 313–340, 1966) and other media recommended by Waksman (The Actinomycetes, vol. II, The Williams and Wilkins Co., 1961). The cultural characteristics were determined after 6 to 14 days of incubation at 30° C.

Table 5

The number of some of the culture media refers to those given by Shirling and Gottlieb

| Culture Medium | Cultural Characteristics | |
| --- | --- | --- |
|  | A/10889 | A/6353 |
| Medium n. 2 (Yeast exctract-malt agar) | Abundant growth, wrinkled surface, amber | Abundant growth, slightly wrinkled light orange to light amber |
| Medium n. 3 (Oatmeal agar) | Moderate growth, smooth, opaque, cream to orange at edges | Abundant growth, with smooth and thin surface, light orange. Some sporangia, hight yellow soluble pigment |
| Medium n. 4 (Inorganic salts-starch agar) | Moderate growth, smooth surface, deep orange | Abundant growth with smooth surface orange. Some sporangia. Canary yellow soluble pigment |
| Medium n. 5 (Glycerol-asparagine agar) | Moderate growth, smooth surface, orange | Abundant growth with smooth surface, light orange. Abundant production of pigment. Canary yellow soluble pigment |
| Medium n. 6 (Peptone-yeast exctract-iron agar) | Scanty growth, rough surface, dark brown, with brown pigment | Moderate growth with smooth surface orange |
| Medium n. 7 (Tyrosine agar) | Abundant growth, crusty surface, coffee colored Weakly brown pigment | Abundant growth with smooth surface, rose amber. Good production of sporangia. Rose amber soluble pigment |
| Oatmeal agar (according to Waksman) | Abundant growth, crusty surface, orange Traces of rudimentary aerial mycelium | Abundant growth, with smooth surface, light orange to topaze yellow Good production of big sporangia, yellow soluble pigment |
| Hickey and Tresner's agar | Abundant growth, wrinkled surface, light brown | Abundant growth with smooth surface rose amber Abundant production of sporangia |
| Czapek glucose agar | Poor growth, smooth surface, light orange Traces of rudimentary aerial mycelium | Abundant growth with smooth and thin surface, orange Abundant production of sporangia |
| Glucose asparagine agar | Abundant growth, crusty surface, deep orange | Abundant growth with smooth surface orange. Some sporangia |
| Nutrient agar | Moderate growth, crusty surface, orange to light brown | Abundant growth with smooth surface, orange |
| Potato agar | Abundant growth, wrinkled surface, orange to light brown. Traces of rudimentary aerial mycelium | Abundant growth, with smooth surface amber |
| Bennett's agar | Abundant growth, wrinkled surface, light orange. | Abundant growth with crusty surface light orange |
| Calcium malate agar | Moderate growth, crusty surface, cream to light orange. | Scarce growth with smooth surface. colorless. Some sporangia |
| Skim milk agar | Abundant growth, wrinkled surface, deep orange. | Abundant growth with slightly crusty surface, deep orange yellow soluble pigment |
| Czapek agar | Poor growth, crusty surface, light orange | Scarce growth light orange Moderate production of sporangia |
| Egg agar | Abundant growth, smooth surface, orange | Abundant growth, with smooth surface, light creme. Moderate production of sporangia |
| Peptone glucose agar | Very scant growth, smooth surface, hyaline | Abundant growth, with wrinkled surface, deep orange |
| Agar | Very scanty growth, thin and smooth hyaline | Very scanty growth thin and smooth. Colorless |

Table 5-continued

The number of some of the culture media refers to those given by Shirling and Gottlieb

| Culture Medium | Cultural Characteristics | |
|---|---|---|
| | A/10889 | A/6353 |
| Loeffler serum | Very scanty growth, smooth surface, light orange to amber | Scarce growth, light orange |
| Potato | Scanty growth, wrinkled surface, orange | Scarce growth, wrinkled, light orange |

The most convenient temperature for development of the colonies was found to range from about 18° to about 42° C, the optimum temperature being from about 28° to about 37° C.

Table 6 reports the utilisation of carbon sources examined according to the method of Pridham and Gottlieb.

Table 6

Carbon Utilization

| Carbon source | Growth | |
|---|---|---|
| | A/10889 | A/6353 |
| Inositol | − | + |
| Fructose | + | + |
| Rhamnose | + | + |
| Mannitol | + | − |
| Xylose | + | + |
| Raffinose | − | − |
| Arabinose | + | + |
| Cellulose | − | − |
| Salicin | + | − |
| Sucrose | + | − |
| Mannose | + | + |
| Lactose | + | − |
| Glucose (positive control) | + | + |

Table 7 reports physiological characteristics of the two strains.

Table 7

Physiological characteristics

| Test | A/10889 | A/6353 |
|---|---|---|
| Starch hydrolysis | positive | positive |
| $H_2S$ formation | positive | negative |
| Melanin production | positive | negative |
| Tyrosine hydrolysis | positive | negative |
| Casein hydrolysis | negative | positive |
| Ca-malate hydrolysis | negative | negative |
| Litmus milk coagulation | negative | negative |
| Litmus milk peptonization | negative | negative |
| Nitrate reduction | positive | negative |
| Gelatin liquefaction | positive | negative |

The two strains A/6353 and A/10889 because of their global sporangia, motile spores and colony morphology are ascribed to the genus Actinoplanes. However, they are clearly different from each other on the basis of their growth pattern on different agars, production or non-production of soluble pigment, carbon utilization pattern, and physiological characteristics. In particular, A/6353 shows a very limited ability to hydrolize glycosidic bonds, including sucrose which is utilized by all the species of Actinoplanes so far described. A/10889 produces a rudimentary aerial mycelium, seldom found in Actinoplanes species. The two strains are also easily distinghishable from all the Actinoplanes species so far known. For these reasons, strain A/6353 and strain A/10889 are recognized as new species of Actinoplanes and are given the names *Actinoplanes liguriae* ATCC 31048 and *Actinoplanes garbadinensis* ATCC 31049.

EXAMPLE 1

Production of the antibiotic, isolation and separation of the various metabolities For producing the antibiotic activities the strain *Actinoplanes Garbadinensis* ATCC 31049 is aerobically pre-cultured in a nutrient medium until substantial antibiotic activity is present. As an example a shake flask culture may have the following composition in g/l.

| | |
|---|---|
| Meat extract | 3.0 |
| Yeast extract | 10.0 |
| Calcium carbonate | 4.0 |
| Starch | 25.0 |
| Tap water q.s. to 1000 ml. | |

The flasks are shaken for about 24 hours at about 28°–30° C an then the pre-cultures (1 liter) are used to inoculate jar fermentors each containing 10 liters of the following nutrient medium:

| | |
|---|---|
| Meat extract | 40 g |
| Peptone | 40 g |
| Yeast extract | 10 g |
| Sodium chloride | 25 g |
| Soybean meal | 100 g |
| Glucose | 500 g |
| Calcium carbonate | 50 g |
| Tap. water q.s. to 10 liters | |

The fermentation batches are incubated aerobically under stirring at 28°–30° C. At intervals the antibiotic activity is assayed microbiologically by the agar diffusion method using *Sarcina lutea* as the test organism. The maximum activity is reached after 96–120 hours of fermentation.

The fermentation broth is adjusted at pH 8.0 and then filtered using Hyflo super-cell as a filter aid. The mycelium is discarded and the filtrate is extracted with an amount of butanol corresponding to about one-half of its volume. The organic phase is separated from the aqueous one, and, after washing with acidic water (pH 4.0) is concentrated to about one-tenth of its original volume and allowed to stand for 10–12 hours at a temperature of 3°–6° C. A crude precipitate forms, which is collected on filter, washed with butanol and dried under vacuum at room temperature: yield 3.0 g. Chromatographic assays on Whatman paper No. 1 or on silica-gel of this crude precipitate, and subsequent microbiological development of the spots by using *Staphylococcus aureus* as the detecting system, indicate the presence of two components which are defined as metabolite A and metabolite B (gardimycin): they have different $R_f$ values which depend on the nature of the employed eluting system.

The crude mixture is further purified by dissolving in about 30 ml. of water. The resulting solution is dialyzed for about 16 hours against distilled water and then concentrated to small volume under vacuum. 1.5 Grams of rough antibiotic substance are obtained, which still is a mixture of metabolite A and gardimycin. The two antibiotic substances are separated and purified by several countercurrent extractions, by relying upon the different partition coefficients of component A and gardimycin in the predetermined solvent system. The employed solvent system consists of butanol:sodium-potassiumphosphate buffer M/15 pH 7.2: hexane in the ratio 1:1:0.1; the partition coefficients in this medium of metabolite A and gardimycin are 0.3 and 0.8 respectively. After 100 extractions, 0.450 g. of gardimycin as its monosodium salt are obtained.

The mother liquors from the butanol extract after precipitation of the mixture of metabolites A and B are further concentrated to small volume and then poured into an excess of light petroleum. A precipitate readily forms, which is recovered by filtration. Chromatographic assays carried out under the same conditions as before indicate that this fraction consists of one product which has different $R_f$ value from metabolites A and B in the same eluting systems. This fraction is named metabolite C.

The different chromatographic-patterns of the three metabolities in the various eluting systems are reported in the following table:

acid 6N at 120° in a closed funnel for 16 hours and chromatographic analysis of the hydrolysis products it was possible to evidence the following amino-acids; valine, serine, glycine, glutamic acid, isoleucine, leucine and alanine. After alkaline hydrolysis with barium hydroxide at 110° in a closed funnel for 15 hours and chromatographic analysis of the hydrolysis products it is possible to evidence the presence of tryptophane. The above mentioned amino-acids are present in the following ratio:

| Amino-acids | Approximate ratio |
|---|---|
| Valine | 2 |
| Serine | 1 |
| Glycine | 2 |
| Glutamic acid | 1 |
| Isoleucine | 2 |
| Leucine | 1 |
| Alanine | 1 |
| Tryptophan | 1 |

Moreover, the analysis of the products resulting from the acidic hydrolysis reveals the presence of further amino-acids of undetermined structure, some of them containing sulfur. Furthermore, gardimycin (as the monosodium salt) is characterized by the following properties:

Chromatographic patterns of metabolite A, metabolite B (gardimycin) and metabolite C.

Chromatography on Whatman paper No. 1
Visualization of the spots by microbiological development on *Staphylococcus aureus*

| ELUTING SYSTEM | $R_f$ values | | |
|---|---|---|---|
| | Metabolite A | Metabolite B (gardimycin)* | Metabolite C |
| 1) Butanol saturated with phosphate buffer M/15 pH 6.0 | 0.00 | 0.15 | 0.85 |
| 2) Butanol saturated with water containing 2% of p-toluenesulfonic acid | 0.75 | 0.80 | 0.95 |
| 3) Butanol saturated with water containing 2% of ammonium hydroxide | 0.15 | 0.10 | 0.85 |
| 4) Phosphate buffer M/15 pH. 6.0 saturated with butanol | 0.65 | 0.80 | 0.00 |
| 5) 20% aqueous solution of sodium chloride | 0.00 | 0.80 | 0.00 |
| 6) Butanol:methanol:water=40:10:20 with 0.75% of methyl orange | 0.70 | 0.65 | 0.90 |
| 7) Butanol:methanol:water=40:10:20 | 0.85 | 0.60 | 0.90 |
| 8) Acetone:water=1:1 | 0.80 | 0.80 | 0.65 |
| 9) Ethyl acetate saturated with water | 0.00 | 0.00 | 0.75 |

Thin-layer chromatography on silicagel.
Visualization of the spots by sulfuric acid and vanilline and microbiological development on *Staphylococcus aureus*

| ELUTING SYSTEM | | | |
|---|---|---|---|
| Ammonium hydroxide:ethanol:water=1:8:1 | 0.30 | 0.70 | 0.00 |

*Metabolite B is tested as the monosodium salt

EXAMPLE 2

By operating as described in Example 1 the strain *Actinoplanes Liguriae* ATCC 31048 is aerobically cultivated for 130–170 hours at about 28°–30° C. 1.4 Grams of antibiotic activity are obtained, which are a mixture of metabolitie A and metabolite B (gardimycin). The existence of the two metabolites has been detected by means of the same chromatographic assays reported in Example 1. The purification of the obtained antibiotic activity and the separation of the two metabolites has been achieved as in Example 1. 0.2 Grams of gardimycin as the monosodium salt are obtained.

Chemico-physical properties of gardimycin as the monosodium salt

Gardimycin (as the monosodium salt) is an amorphus white powder with amphoteric character. It has an isoelectric point of 4.2 which was determined by electrofocalization. Upon strong hydrolysis in hydrochloric 1. Melting point: 260° C (decomposition).
2. Molecular weight: 2005–2168.
3. Elemental analysis: C = 48.7–48.6%; H = 6.7–6.6%; N=11.8–12.2%; S = 5.3–5.5%; Na = 1.1%; $H_2O$ = 3.6–3.3%.
4. U.V. absorpion bands: In each of the below outlined solvent systems, gardimycin shows the following values:

| Solvent | $\lambda$ (m$\mu$) max | $E_1^{1\%}$ cm. |
|---|---|---|
| methanol | 273 (shoulder) | |
| | 280 | 26 |
| | 299 | 24 |
| sodium hydroxide 0.1N | 273 (shoulder) | |
| | 279 | 26 |
| | 288 | 22 |
| hydrochloric acid 0.1N | 273 (shoulder) | |
| | 279 | 26 |
| | 288 | 22 |
| phosphate buffer pH. 7.38 | 273 (shoulder) | |
| | 279 | 24 |

| Solvent | λ (mμ) max | $E_1^{1\%}$ cm. |
|---|---|---|
| | 288 | 20 |

The complete picture of the spectrum is given in FIG. 1.

5. Infrared spectrum: Characteristic absorption bands in nujol have been observed at the following frequencies: (Cm$^{-1}$): 3280, 2920–2840 (nujol); 1650, 1520, 1455 (nujol), 1375 (nujol), 1260, 1045, 990, 720.

Figure 2:
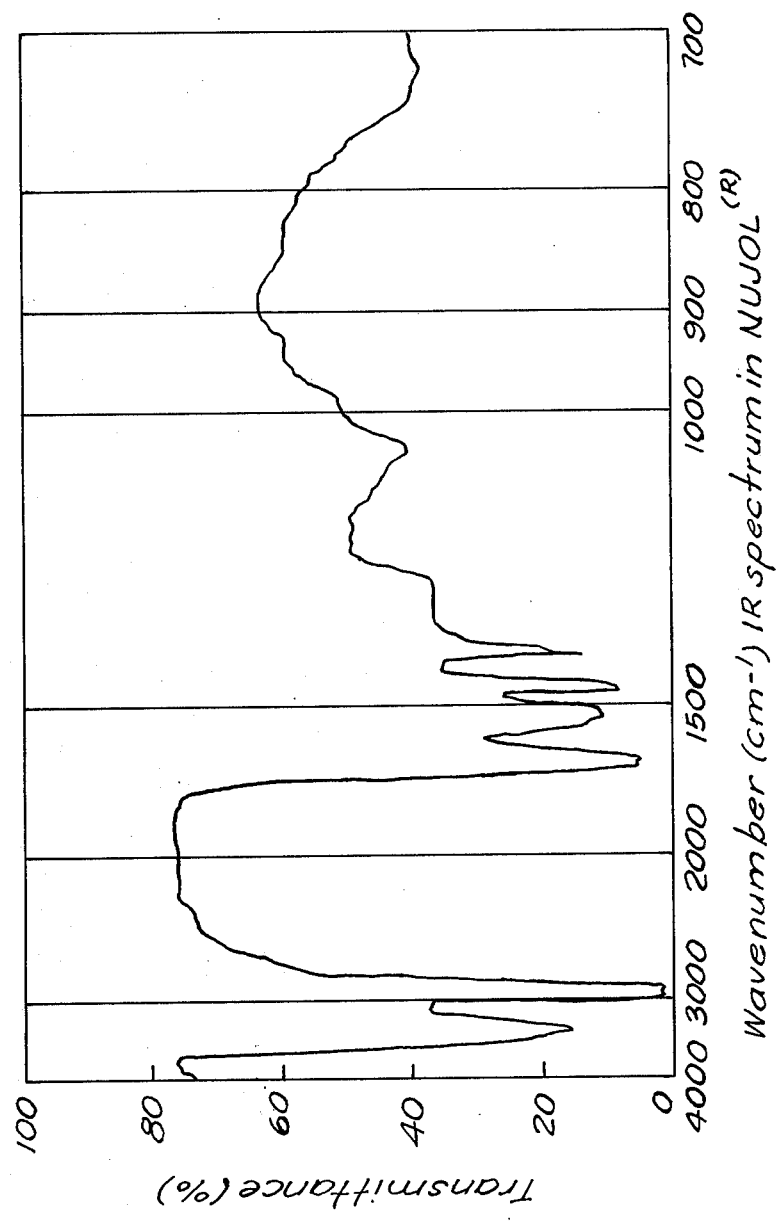

The complete picture of the spectrum is given in FIG. 2.

6. Specific rotation: $[\alpha]_D^{25} = -44°$ (c = 0.5% dimethylformamide).

7. Solubility: soluble in water, aqueous sodium bicarbonate, diluted aqueous solutions of alkali hydroxides, hot methanol, dimethylformamide, dimethylsulfoxide, glacial-acetic acid. Insoluble in diluted mineral acids, benzene, acetone, chloroform, carbon tetrachloride, ($C_{2-6}$)-aliphatic alkanols, tetrahydrofuran.

8. Characteristic reactions:

| Fehling | positive |
|---|---|
| Tollens | positive |
| KMnO$_4$ | positive |
| H$_2$SO$_4$ conc. | positive |
| Ninhydrin | negative |
| FeCl$_3$ | negative |
| Millon | negative |
| Schiff | negative |
| Maltol | negative |

9. Ionizable functions: An ionizable function is potentiometrically evidenced with pK$_a$ =7.1 (water) and pK$_a$=8.5 (methylcellosolve:water: 16:4).

10. Furthermore, starting from the monosodium salt of gardimycin it is possible to prepare the following derivatives:

a. Gardimycin free acid: 1.0 g of gardimycin monosodium salt is dissolved in 150 ml. of water. The resulting solution is brought to pH 2.5 by adding aqueous 10% hydrochloric acid and is then extracted two times with 75 ml. of butanol saturated with water. The butanol extracts are collected and concentrated in vacuo at 45° C to a volume corresponding to 1/20 of the initial volume. After standing at 4° C for 12 hours a precipitate forms, which is collected, washed with light petroleum and dried in vacuo at 40°–45° C. 0.950 Grams of product are obtained which decomposes between about 250° and about 300° C.

b. Gardimycin disodium salt: 1.0 g. of gardimycin monosodium salt is dissolved in 150 ml. of water and the pH of the resulting solution is brought to 9.6 by adding N/10 sodium hydroxide. The solution is then lyophilized. 0.900 Grams of product are obtained melting at 250° C.

c. Gardimycin calcium salt: 0.3 g. of gardimycin monosodium salt are dissolved in 20 ml. of water and the resulting solution is slowly added, under stirring, with several portions of a saturated solution of calcium chloride until a complete precipitation is reached. The obtained solid id filtered, dried in vacuo and dissolved in 10 ml. of acetone. After pouring into 200 ml. of diethylether a precipitate forms, which is filtered and dried in vacuo at 40°–45° C. 0.2 Grams of product are obtained which decomposes at 330°–40° C.

We claim:

1. A process for producing Gardimycin which comprises cultivating a strain selected from the group consisting of *Actinoplanes garbadinensis* ATTCC 31049 and *Actinoplanes liguriae* ATCC 31048 under aerobic conditions, in an aqueous nutrient medium containing an assimilable source of carbon, an assimilable source of nitrogen and inorganic salts, until a substantial antibiotic activity is present in the medium, recovering said antibiotic activity therefrom, and separating it from the medium.

2. A process as defined in claim 1, wherein the fermentation is carried out at a temperature between about 25° and about 35° C.

3. A process as defined in claim 1, wherein the fermentation is carried out for a time ranging from about 96 to 170 hours.

4. The antibiotic substance gardimycin having the following characteristics (as the monosodium salt):

1. Melting point: 260° C (decomposition);
2. Molecular weight: 2005–2168;
3. Elemental analysis: C=48.7–48.6%; H=6.7–6.6% N=11.8–12.2%; S=5.3–5.5%; Na=1.1%; H$_2$O=3-.6–3.3%;
4. U.V. absorption bands: In each of the below outlined solvent systems, gardimycin shows the following values:

| Solvent | λ(m) max | $E_1^{1\%}$ cm. |
|---|---|---|
| methanol | 273 (shoulder) | |
| | 280 | 26 |
| | 299 | 24 |
| sodium hydroxide 0.1N | 273 (shoulder) | |
| | 279 | 26 |
| | 288 | 22 |
| hydrochloric acid 0.1N | 273 (shoulder) | |
| | 279 | 26 |
| | 288 | 22 |
| phosphate buffer pH. 7.38 | 273 (shoulder) | |
| | 279 | 24 |
| | 288 | 20 |

The complete picture of the spectrum is given in FIG. 1;

5. Infrared spectrum: characteristic absorption bands in nujol have been observed at the following frequencies (cm$^{-1}$): 3280, 2920–2840 (nujol), 1650, 1520, 1455 (nujol), 1375 (nujol), 1260, 1045, 990, 720;

The complete picture of the spectrum is given in FIG. 2;

6. Specific rotation: $[\alpha] = -44°$ (c = 0.58% dimethylformamide);

7. Solubility: soluble in water, aqueous sodium bicarbonate, diluted aqueous solutions of alkali hydroxides, hot methanol, dimethylformamide, dimethylsulfoxide, glacial-acetic acid. Insoluble in diluted mineral acids, benzene, acetone, chloroform, carbon tetrachloride, ($C_{2-6}$)-aliphatic alkanols, tetrahydrofuran;

8. Characteristic reactions:

| Fehling | positive |
|---|---|
| Tollens | positive |
| KMnO$_4$ | positive |
| H$_2$SO$_4$conc. | positive |
| Ninhydrin | negative |

| | |
|---|---|
| FeCl₃ | negative |
| Million | negative |
| Schiff | negative |
| Maltol | negative |

9. Ionizale functions: an ionizable function is potentiometrically evidenced with $pK_a = 7.1$ (water) and $pK_a = 8.5$ (methylcellosolve:water= 16:4);

10. Isoelectric point: 4.2 (determined by electrofocalization);

11. $R_f$ values:

| Chromatography on Whatman paper No. 1 Visualization of the spots by microbiological development on *Staphyloccus aureus* ELUTING SYSTEM | $R_f$ values |
|---|---|
| 1) Butanol saturated with phosphate buffer M/15 pH 6.0 | 0.15 |
| 2) Butanol saturated with water containing 2% of p-toluenesulfonic acid | 0.80 |
| 3) Butanol saturated with water containing 2% of ammonium hydroxide | 0.10 |
| 4) Phosphate buffer M/15 pH 6.0 saturated with butanol | 0.80 |
| 5) 20% aqueous solution of sodium chloride | 0.80 |
| 6) Butanol:methanol:water=40:10:20 with 0.75% of methyl orange | 0.65 |
| 7) Butanol:methanol:water=40:10:20 | 0.60 |
| 8) Acetone:water=1:1 | 0.80 |
| 9) Ethyl acetate saturated with water | 0.00 |

Thin-layer chromatography on silicagel. Visualization of the spots by sulfuricacid and vanilline and microbiological development on *Staphylococcus aureus*

ELUTING SYSTEM

Ammonium hydroxide:ethanol-water=1:8:1

The antibiotic being further characterized by the following approximate ratio of amino-acids of identified structure:

| Amino-acid | Approximate ratio |
|---|---|
| Valine | 2 |
| Serine | 1 |
| Glycine | 2 |
| Glutamic acid | 1 |
| Isoleucine | 2 |
| Leucine | 1 |
| Alanine | 1 |
| Tryptophan | 1 |

5. The antibiotic substance gardimycin a defined in claim 4 as the free acid.

6. The antibiotic substance gardimycin as defined in claim 4 as the disodium salt.

7. The antibiotic substance gardimycin as defined in claim 4 as the calcium salt.

* * * * *